US012766307B2

(12) United States Patent
Curran et al.

(10) Patent No.: US 12,766,307 B2
(45) Date of Patent: Oct. 20, 2026

(54) BLOOD PUMP BLOOD COMPATIBILITY DEVICE

(71) Applicant: ABIOMED, Inc., Danvers, MA (US)

(72) Inventors: Jerald Curran, Danvers, MA (US); Jin Kwang Kim, Danvers, MA (US); Jeremy Moretz, Danvers, MA (US); Claudia Mourran, Aachen (DE)

(73) Assignee: ABIOMED, INC., Danvers, MA (US)

(*) Notice: Subject to any disclaimer, the term of this patent is extended or adjusted under 35 U.S.C. 154(b) by 351 days.

(21) Appl. No.: 18/122,775

(22) Filed: Mar. 17, 2023

(65) Prior Publication Data

US 2023/0293879 A1 Sep. 21, 2023

Related U.S. Application Data

(60) Provisional application No. 63/321,437, filed on Mar. 18, 2022.

(51) Int. Cl.
*A61M 60/523* (2021.01)
*A61M 60/178* (2021.01)
(Continued)

(52) U.S. Cl.
CPC ........ *A61M 60/523* (2021.01); *A61M 60/178* (2021.01); *A61M 60/216* (2021.01);
(Continued)

(58) Field of Classification Search
CPC .............. A61M 60/523; A61M 60/585; A61M 60/589; A61M 60/546; A61M 60/178; A61M 60/216
See application file for complete search history.

(56) References Cited

U.S. PATENT DOCUMENTS

2005/0015001 A1 1/2005 Lec et al.
2005/0245831 A1 11/2005 Banet
(Continued)

FOREIGN PATENT DOCUMENTS

AU 2018239421 A1 10/2019
AU 2018279862 A1 12/2019
(Continued)

OTHER PUBLICATIONS

International Search Report and Written Opinion for corresponding PCT Application No. PCT/US2023/015440, dated Jul. 3, 2023.
(Continued)

*Primary Examiner* — Lindsey G Wehrheim
(74) *Attorney, Agent, or Firm* — MEAGHER EMANUEL LAKS GOLDBERG & LIAO, LLP

(57) ABSTRACT

Systems and method are disclosed involving a pump control module configured to control an intravascular blood pump and display information about the intravascular blood pump, and a blood monitoring module configured to derive a value of a blood parameter from information received about a blood sample, such as information received from a blood monitoring sensor, and display the value of the blood parameter on the first display screen and/or on a second display screen. The system and method may also include predicting other parameters based on, e.g., the information received from the blood sample. The predictions may include, e.g., predictions of heart failure or bleeding events.

15 Claims, 10 Drawing Sheets

(51) Int. Cl.

| | |
|---|---|
| ***A61M 60/216*** | (2021.01) |
| ***A61M 60/546*** | (2021.01) |
| ***A61M 60/585*** | (2021.01) |
| ***A61M 60/859*** | (2021.01) |

(52) U.S. Cl.
CPC ........ *A61M 60/546* (2021.01); *A61M 60/585* (2021.01); *A61M 60/859* (2021.01)

(56) References Cited

U.S. PATENT DOCUMENTS

| | | | | |
|---|---|---|---|---|
| 2009/0156922 | A1 | 6/2009 | Goldberger et al. | |
| 2019/0269840 | A1* | 9/2019 | Tuval .................. | A61M 60/139 |

FOREIGN PATENT DOCUMENTS

| | | | |
|---|---|---|---|
| AU | 2020282983 | A1 | 2/2022 |
| AU | 2020301227 | A1 | 2/2022 |
| WO | 20170048733 | A1 | 3/2017 |
| WO | 2018227156 | A1 | 12/2018 |

OTHER PUBLICATIONS

Shore-Lesserson et al., "Thromboelastography-Guided Transfusion Algorithm Reduces Transfusions in Complex Cardiac Surgery", Anesthesia & Analgesia, vol. 88, Issue 2, pp. 312-319. Feb. 1999.

Sun et al., "Thromboelastography (TEG)-Based Algorithm Reduces Blood Product Utilization in Patients Undergoing VAD Implant", Journal of Cardiac Surgery, vol. 29, Issue 2, pp. 238-243, Feb. 11, 2014.

ESSR corresponding to EP Application No. 23771431.6, issued Feb. 20, 2026.

Canadian Office Action and Search Report for corresponding CA Application No. 3,246,080, dated Jul. 13, 2026.

* cited by examiner

BLOOD PUMP BLOOD COMPATIBILITY DEVICE

CROSS-REFERENCE TO RELATED APPLICATIONS

The present application claims priority to U.S. Provisional Patent Application No. 63/321,437, filed Mar. 18, 2022, the contents of which are incorporated by reference herein in it entirety.

TECHNICAL FIELD

Embodiments disclosed herein relate to medical devices, such as intravascular blood pumps, and devices and methods for monitoring and/or controlling blood coagulation.

BACKGROUND

When medical devices, such as intravascular blood pumps, are utilized, it is useful to attempt to monitor and control of blood coagulation. For example, it may useful to monitor and control blood coagulation as the human blood will naturally coagulate due to contact pathway activation when blood-contacting medical devices are introduced. Typically, control of blood coagulation is achieved by providing controlled dosages of anticoagulants. Too much anticoagulant may result in a bleeding event, which may be an unacceptable result when using a blood pump, while too little anticoagulant may run the risk of the clotting and thrombus formation, which also may be undesirable.

Intravascular blood pumps can be introduced into a patient either surgically or percutaneously and used to deliver blood from one location in the heart or circulatory system to another location in the heart or circulatory system. For example, when deployed in the left heart, an intravascular blood pump can pump blood from the left ventricle of the heart into the aorta. Likewise, when deployed in the right heart, an intravascular blood pump can pump blood from the inferior vena cava into the pulmonary artery. Examples of such blood pumps include the IMPELLA® family of devices (Abiomed, Inc., Danvers, MA).

BRIEF SUMMARY

To provide useful, rapid testing, new systems and techniques are disclosed.

A first aspect is drawn to a system that may include a patient console having a first housing with a first display screen, a pump control module at least partially disposed within the first housing, and a blood monitoring module. The pump control module may be configured to control an intravascular blood pump and display information about the blood pump on the display screen. The blood monitoring module may be configured to derive a value of a blood parameter from information received from a blood monitoring sensor about a blood sample and display the value of the blood parameter on the first display screen and/or on a second display screen.

In some embodiments, the system may include a processor. In some embodiments, the pump control module and the blood monitoring module are operably coupled to the processor. In some embodiments, the processor may comprise a plurality of processors, including a first processor and a second processor. In some embodiments, the first processor may be disposed in or on the pump control module, and the second processor may be disposed in or on the blood monitoring module. In some embodiments, the processor is disposed only within the first housing.

In some embodiments, the blood monitoring module may be within the first housing. In some embodiments, the system may include a blood monitoring console. The blood monitoring module may have a second housing. The second housing may have a second display screen. In some embodiments, the blood monitoring module may be disposed in the second housing. In some embodiments, the blood monitoring console may be coupled to the patient console. In some embodiments, the blood monitoring console may be removably coupled to the first housing. In some embodiments, the blood monitoring module may be disposed at least partially in the first housing.

In some embodiments, the system may include a first port configured to receive the blood sample. The blood sample may be received in a variety of ways. In some embodiments, the first port may be configured to removably receive a cartridge containing the blood sample. In some embodiments, the first port may be configured to be operably coupled to a catheter or tube. In some embodiments, the catheter or tube may be configured to contain electrical connections to the blood pump and/or to an access delivery device (e.g., a delivery sheath) in addition to allowing blood to be transported therethrough. In some embodiments, the catheter or tube may be operably connected to a patient at a different location than an insertion point of the intravascular blood pump, wherein the catheter is configured to transfer the blood sample from the patient to the first port. In some embodiments, the catheter or tube may be operably connected to the intravascular blood pump, wherein the catheter is configured to transfer the blood sample from the patient to first port.

In some embodiments, the blood monitoring sensor may be configured to sense the blood parameter of the blood sample received in the first port. In some embodiments, the first port may be disposed in a blood monitoring console coupled to the patient console or disposed in the patient console.

In some embodiments, the system may include a second port configured to allow blood to exit the housing. In some embodiments, the second port may be connected to a waste stream.

In some embodiments, the blood monitoring sensor is located remotely from the blood monitoring module. In some embodiments, the blood monitoring sensor is disposed on the intravascular blood pump. In some embodiments, the blood monitoring sensor is disposed on a removable patch on a patient's skin.

In some embodiments, the blood parameter may comprise or relate to blood coagulation. In some embodiments, the blood parameter may include a prothrombin time (PT), an activated clotting time (ACT), a clot propagation rate, a clot strength, a rate of clot breakdown, a platelet mapping, a functional fibrinogen, and/or a fibrin polymerization. In some embodiments, the blood parameter may include an international normalized ratio (INR).

A second aspect is drawn to a system that may include a pump control module configured to control an intravascular blood pump, and one or more processors. The one or more processors may operably communicate with the pump control module. The one or more processors may be within a patient console and/or a blood monitoring console.

The one or more processors configured with instructions that, when executed by the one or more processors, cause the system to perform specific tasks. Such tasks may include receiving information about a blood sample from a sensor, determining a value of a blood parameter based on the information about the blood sample, and displaying the value of the blood parameter on the first display screen and/or on a second display screen.

In some embodiment, the one or more processors may be configured with instructions that, when executed, cause the system to receive the blood sample. In some embodiments, the processor may comprise a plurality of processors, including a first processor and a second processor. In some embodiments, the first processor may be disposed in or on the pump control module, and the second processor may be disposed in or on the blood monitoring module. In some embodiments, the processor is disposed only within the first housing.

In some embodiments, the pump control module may be at least partially disposed in a first housing. In some embodiments, the blood monitoring module may be disposed at least partially in the first housing. In some embodiments, the blood monitoring module may be within the first housing. In some embodiments, the blood monitoring module may be disposed in a second housing with the second display screen. In some embodiments, the second housing may be coupled to the first housing. In some embodiments, the second housing may be removably coupled to the first housing.

In some embodiments, the one or more processors may be configured to cause a blood sample to be transported to the blood monitoring console. In some embodiments, the blood sample may be retrieved by an intravascular blood pump. In some embodiments, the blood sample may be transported to the housing via a catheter.

In some embodiments, the one or more processors may be configured with instructions that, when executed, cause the system to adjust one or more valves for controlling a flow of the blood sample through the system.

In some embodiments, the blood parameter may comprise or relate to blood coagulation. In some embodiments, the blood parameter may include a prothrombin time (PT), an activated clotting time (ACT), a clot propagation rate, a clot strength, a rate of clot breakdown, a platelet mapping, a functional fibrinogen, and/or a fibrin polymerization. In some embodiments, the blood parameter may include an international normalized ratio (INR).

A third aspect is drawn to a method. The method may include receiving information about the blood sample from a blood monitoring sensor, which may be disposed in a blood monitoring console. The method may include determining a value of a blood parameter based on the received blood sample information, wherein the blood parameter is or relates to blood coagulation. The method may include displaying the value of the blood parameter on a display screen of a patient console and/or a blood monitoring console. The method may include operating a blood pump via a module at least partially disposed in the patient console.

In some embodiments, the method may include controlling the blood pump based on the determined value of the blood parameter.

In some embodiments, the method may include using the value of the blood parameter to predict at least one other parameter, and may also include using a value of a sensor coupled to the blood pump to predict the at least one other parameter. For example, in some embodiments, the other parameter may include a future (e.g., predictive) bleeding event and/or a bleeding complication. In some embodiments, a trained machine learning algorithm is used to predict at least one other parameter. In some embodiments, the trained machine learning algorithm further uses a value from a thromboelastogram to predict the at least one other parameter. In some embodiments, the at least one other parameter may include a prediction of heart failure, such as a prediction of right heart failure. In some embodiments, the prediction of heart failure is made while the blood pump is positioned at least partially within a left ventricle. In some embodiments, the at least one other parameter may include a prediction of a bleeding condition.

In some embodiments, the method may include determining an anticoagulation measure based on the predicted at least one other parameter. In some embodiments, the method may include displaying the anticoagulation measure (e.g., on a first or second display screen). In some embodiments, the method may include automatically enacting the anticoagulation measure. In some embodiments, the anticoagulation measure may include determining or applying a dosage of an anticoagulant, such as heparin or protamine.

In some embodiments, the method may include receiving the blood sample. In some embodiments, receiving the blood sample may include receiving the blood sample in a first port disposed on the patient console or the blood monitoring console. In some embodiments, the blood sample may be in a cartridge or vial. In some embodiments, the first port may be configured to be operably coupled to a catheter or tube. In some embodiments, the catheter may be configured to transfer the blood sample from a patient to the first port. In some embodiments, the method may include obtaining the blood sample via the intravascular blood pump.

In some embodiments, the blood parameter may include a prothrombin time (PT), an activated clotting time (ACT), a clot propagation rate, a clot strength, a rate of clot breakdown, a platelet mapping, a functional fibrinogen, and/or a fibrin polymerization. In some embodiments, the blood parameter may include an international normalized ratio (INR).

A fourth aspect is drawn to a method. The method may include receiving a value of a blood parameter from a blood monitoring sensor of a monitoring patch configured to be disposed on a body of a patient, displaying the value of the blood parameter on a display screen of a patient console, and operating an intravascular blood pump via a module at least partially disposed in the patient console.

In some embodiments, the method may include controlling the blood pump based on the value of the blood parameter.

In some embodiments, the method may include using the value of the blood parameter to predict at least one other parameter, and may also include using a value of a sensor coupled to the blood pump to predict the at least one other parameter. For example, in some embodiments, the other parameter may include a future (e.g., predictive) bleeding event and/or a bleeding complication. In some embodiments, a trained machine learning algorithm is used to predict at least one other parameter. In some embodiments, the trained machine learning algorithm further uses a value from a thromboelastogram to predict the at least one other parameter. In some embodiments, the at least one other parameter may include a prediction of heart failure, such as a prediction of right heart failure. In some embodiments, the prediction of heart failure is made while the blood pump is positioned at least partially within a left ventricle. In some embodiments, the at least one other parameter may include a prediction of a bleeding condition. In some embodiments, the method may include determining an anticoagulation measure based on the predicted at least one other parameter.

In some embodiments, the blood parameter may comprise or relate to blood coagulation. In some embodiments, the blood parameter may include a prothrombin time (PT). In some embodiments, the blood parameter may include an international normalized ratio (INR).

DETAILED DESCRIPTION

Figure 1:
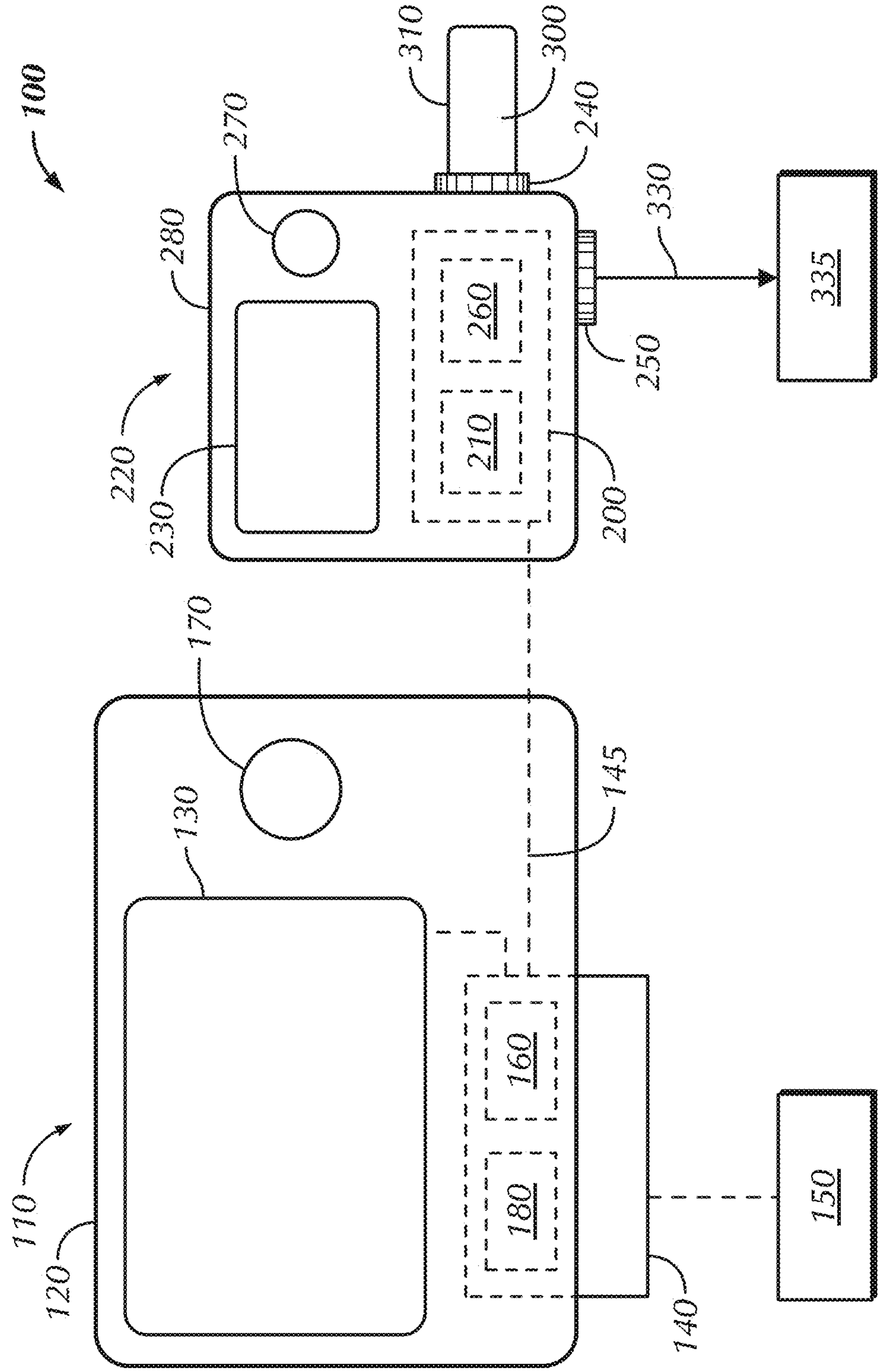
FIG. 1 is schematic illustration of an embodiment of a system.

Embodiments of the present disclosure are described in detail with reference to the figures wherein like reference numerals identify similar or identical elements. It is to be understood that the disclosed embodiments are merely examples of the disclosure, which may be embodied in various forms. Well known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously When medical devices, such as intravascular blood pumps, are utilized, it may be useful to attempt to monitor and control of blood coagulation. For example, the human blood will naturally coagulate due to contact pathway activation when blood-contacting medical devices are introduced. To manage blood coagulation, patients are typically provided controlled dosages of anticoagulants. As will be appreciated, too much anticoagulant may result in a bleeding event, which may be an unacceptable result when using a blood pump, while too little anticoagulant may run the risk of clotting and thrombus formation, which also may ne undesirable.

Unfortunately, current approaches to monitoring coagulation, including activated partially thromboplastic clotting time (aPTT), anti-Xa assays, and thromboelastography (TEG), may take too long, which may make them ineffective in the context of rapidly changing coagulation conditions in critical patients. Also, these conventional techniques may be poorly correlated with bleeding events resulting in anticoagulation protocols that are often imprecise. In view of the above, the inventors have recognized that benefit of new approaches to measuring and managing patient anticoagulation status.

Turning now to the figures, as seen in FIG. 1, in some embodiments, a system 100 may be provided that may include a patient console 110. The patient console may include a housing 120 (e.g., a first housing) with a display screen 130 (e.g., first display screen). In some embodiments, the system 100 also may include a blood monitoring console 220. In such embodiments, the blood monitoring console may include a housing 280 (e.g., second housing). In some embodiments, a display 230 (e.g., a second display) may be disposed within the second housing 280. In some embodiments, the patient console 110 and/or the blood monitoring console 220 may include one or more knobs, buttons, or controls 170, 270 that a user can interact with.

The system 100 may also include a pump control module 140 that may be at least partially disposed within the first housing 120. As described herein, the pump control module may be configured to control an intravascular blood pump 150.

Blood pumps of different types are known, such as axial blood pumps, centrifugal blood pumps, or mixed-type blood pumps, where the blood flow is caused by both axial and radial forces. One such example of a blood pump is the Impella® line of blood pumps (e.g., Impella 2.5®, Impella CP®, Impella 5.5®, etc.), which are products of Abiomed of Danvers. Intravascular blood pumps are insertable into a patient's vessel, such as via the aorta, by means of a catheter.

Such blood pumps may involve the use of numerous medical devices, fluid lines, and the like. These fluid lines may provide necessary fluid to the patient, may be removing or recirculating fluids from the patient (such as blood), or may be providing fluid needed by a medical device, such as a purge fluid. For example, in some blood pumps, a purge fluid may be deployed to keep blood from entering the pump mechanism and to mitigate the effects of blood and/or bio-deposit buildup on the pump mechanisms.

The pump control module may contain all circuitry and components necessary for controlling an intravascular blood pump and receiving information from any sensors in or on the blood pump. For example, the module may include circuitry that controls the electricity that causes the blood pump to rotate, and for receiving information from one or more pressure sensors. The pump control module may also be configured to display information about the blood pump on the display screen 150.

In some embodiments, the system 100 may also include a blood monitoring module 200 configured to derive a value of a blood parameter from information received from a blood monitoring sensor 210 about a blood sample 300. In some embodiments, the blood parameter comprises or relates to blood coagulation (e.g., the blood parameter may be a value that is representative of a degree or amount of blood coagulation, a concentration of a chemical or protein that relates to blood coagulation, etc.).

In some embodiments, the blood parameter may include a prothrombin time (PT). As is known in the art, PT generally relates to the time for plasma to clot after adding a mixture (e.g., a thromboplastin) that comprises tissue factor and a phospholipid to a patient's plasma sample.

Because the same plasma can provide different results based on the composition of the thromboplastin, in some embodiments, the blood parameter may comprise the international normalized ratio (INR). As is known in the art, the INR generally relates to the ratio of the measured PT divided by a control PT value, where the control PT value is obtained using a reference thromboplastin reagent.

In some embodiments, the blood parameter also may include activated clotting time (ACT), a clot propagation rate, a clot strength, a rate of clot breakdown, a platelet mapping, a functional fibrinogen, and/or a fibrin polymerization.

In some embodiments, the blood monitoring module 200 may also be configured to display the value of the blood parameter on the first display screen 130 and/or on the second display screen 230.

In various embodiments and scenarios, there may be different levels of integration between the patient console and the blood monitoring console and/or the blood monitoring module.

In some embodiments, the blood monitoring console 220 may be operably coupled but physically separated from the patient console 110. In some embodiments, the blood monitoring console may be electrically coupled to the patient console. In some embodiments, the blood monitoring console may communicate wirelessly with the patient console.

Figure 2A:
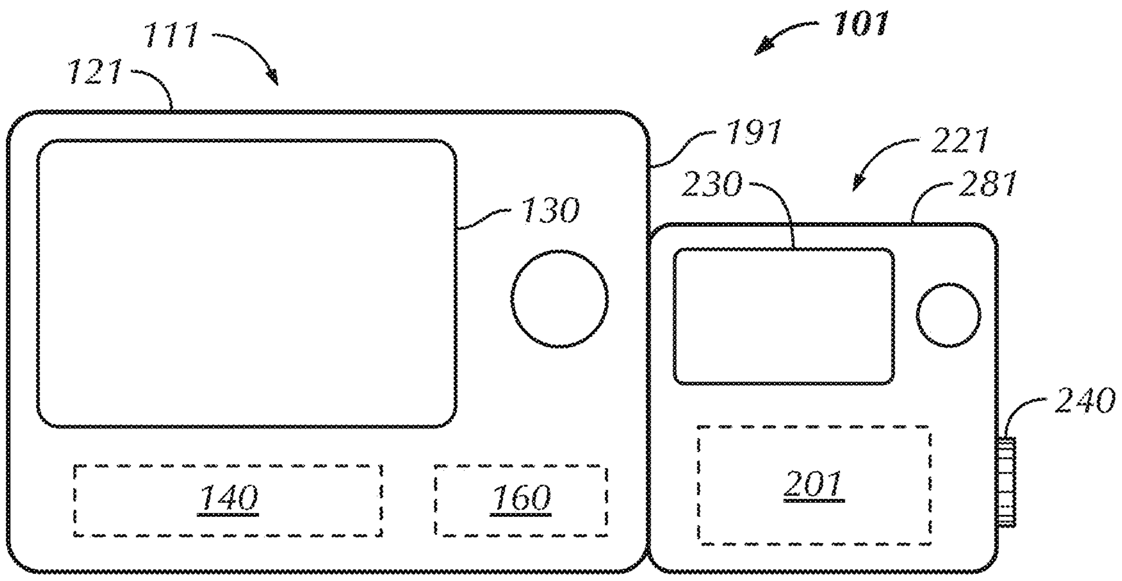
FIGS. 2A and 2B are illustrations of a system where a blood monitoring console is physically coupled to a patient console, where the blood monitoring console has a display (2A) or does not have a display (2B).

As seen in FIG. 2A, in some embodiments, the blood monitoring console 221 may be physically coupled to the patient console 111. In some embodiments, the second housing 281 may be configured to attach to the first housing 121. In some embodiments, the blood monitoring console 221 may be removably coupled to the patient console 111. In some non-limiting examples, a side portion 191 of the first housing 121 contains a slot and locking mechanism such that a portion of the second housing 281 can be removably slid into the slot until it is in a correct position (for example, in a position that allows electrical contacts from each console to connect), and temporarily locked into place until a user presses a button or lever to release the locking mechanism. As will be appreciated, other suitable fasteners may be used to connect the patient console and monitoring consoles together in other embodiments.

In some embodiments, each console may include at least one processor. In some embodiments, the blood monitoring console 221 may include the blood monitoring module 201, but the blood monitoring console 221 may be free of the one or more processors 160, 260. That is, in some embodiments, the processor may be disposed only within the first housing.

Figure 2B:
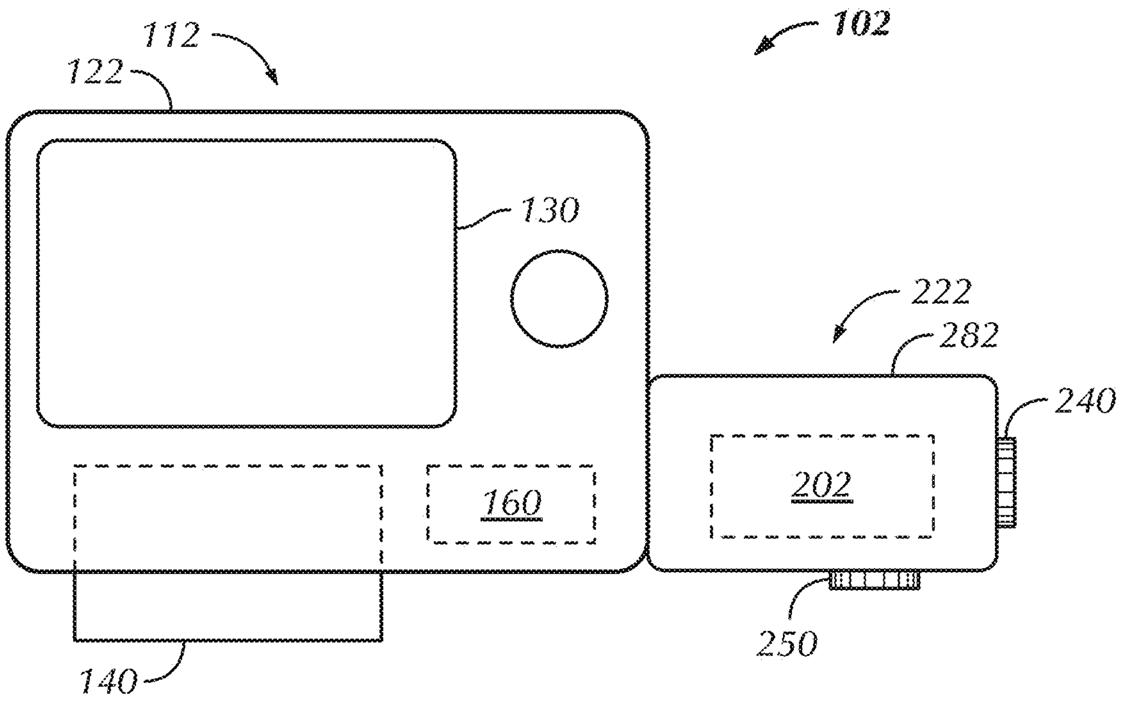

As shown in FIG. 2A, in some embodiments, both the patient console and the blood monitoring console may include displays. As seen in FIG. 2B, in other embodiments, the system 102 may be configured such that the first housing 122 for the patient console 112 has a display 130, but the second housing 282 for the blood monitoring console 222 does not include a display. In some embodiments, the second housing also may be free of the buttons, knobs, or controls 270. In some embodiments, the blood monitoring console 222 may include the blood monitoring module 202, but the blood monitoring console 222 may be free of the one or more processors 160, 260.

Figure 2C:
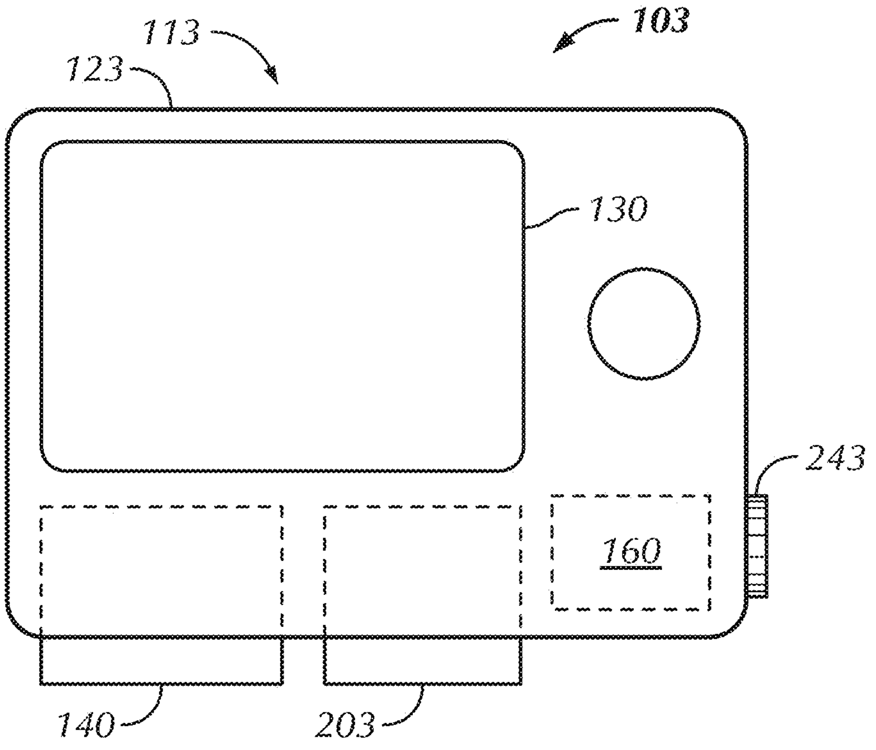
FIG. 2C is an illustration of a system where a blood monitoring console is integrated with a patient console.

As seen in FIG. 2C, in some embodiments, the system may be fully integrated. That is, in some embodiments, the system 103 may be configured such that the blood monitoring module 203 is at least partially within the first housing 123 that defines the patient console 113.

Referring to FIG. 1, in some embodiments, the system 100 may include a first port 240 configured to receive a blood sample 300. In some embodiments, the first port may be disposed in the blood monitoring console 220 coupled to the patient console (see, e.g., FIGS. 2A and 2B). In some embodiments, the first port 240 may be configured to removably receive a cartridge 310 (including, e.g., a vial) containing the blood sample 300. Referring to FIG. 2C, in some embodiments, the first port 243 may be disposed in the patient console 113.

Figure 2D:
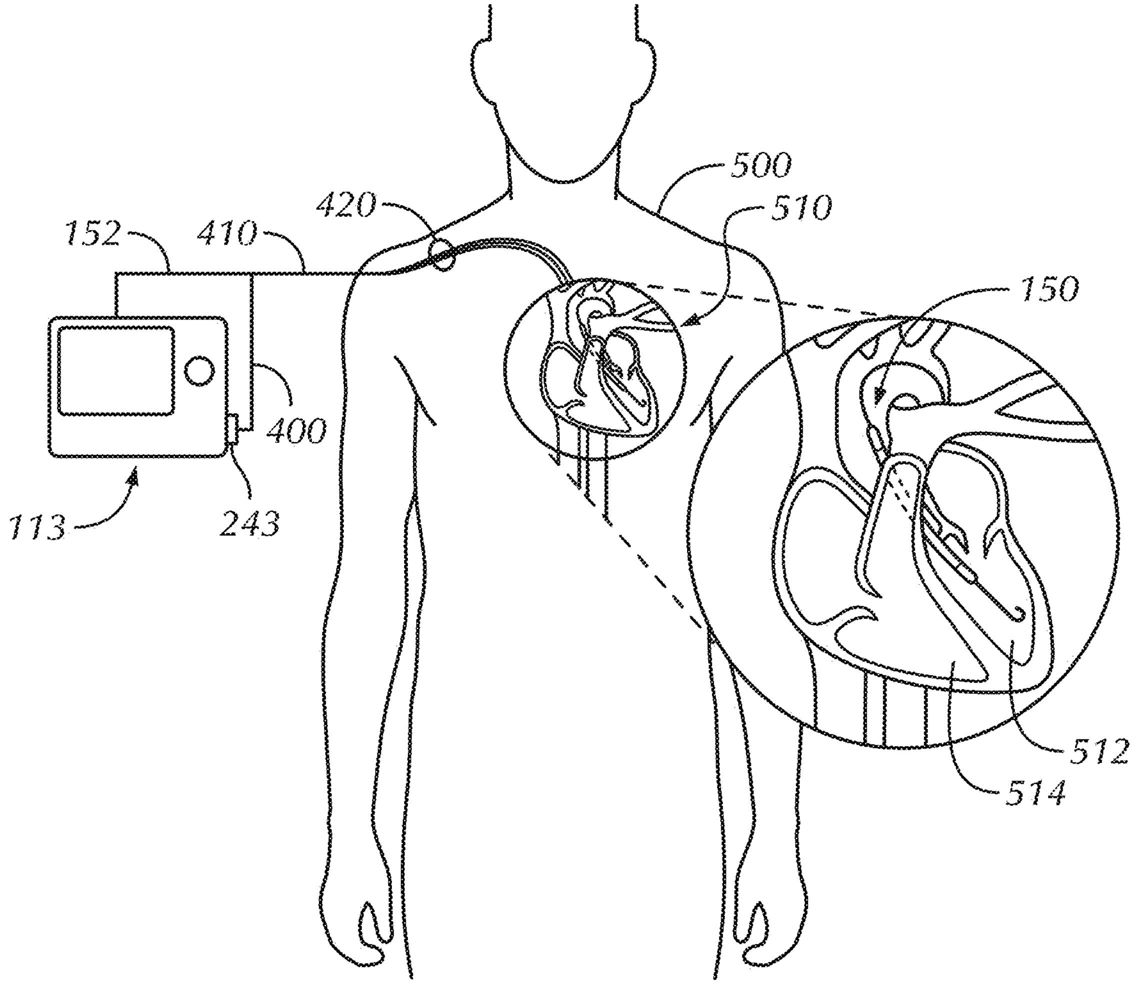
FIGS. 2D and 2E are illustrations of a system coupled to an intravascular heart pump introduced to a patient at a first insertion point, where a blood sample may be captured through the first insertion point (2D) or a second insertion point (2E).

Referring to FIG. 2D, in some embodiments, the first port 243 may be configured to be operably coupled to a catheter or tube 400. For example, in some embodiments, the intravascular heart pump 150 may be positioned in the heart 510 of a patient 500. In some embodiments, the blood sample may be captured by the blood pump 150 and transported through the catheter 400 to the patient console 113, for example. That is, in some embodiments, the catheter or tube 400 may be operably connected to the intravascular blood pump 150, where the catheter or tube 400 is configured to transfer a blood sample from the patient to first port 243. In an illustrative example, an inlet port on the blood pump may draw in blood from the patient and into the blood pump, which would then be available for transport to the patient console 113.

In some embodiments, the catheter or tube 400 may be configured such that at least a portion 410 of the catheter or tube contain electrical connections 152 to the blood pump 150.

As another illustrative example, the tube or catheter may be connected to an access delivery device (e.g., an access sheath), with the blood sample being drawn from another portion of the body (e.g., an artery near a delivery site of the intravascular blood pump). In such embodiments, the catheter or tube 400 may be operably connected to a patient 500 at the insertion point 420 of the intravascular blood pump 150.

Figure 2E:
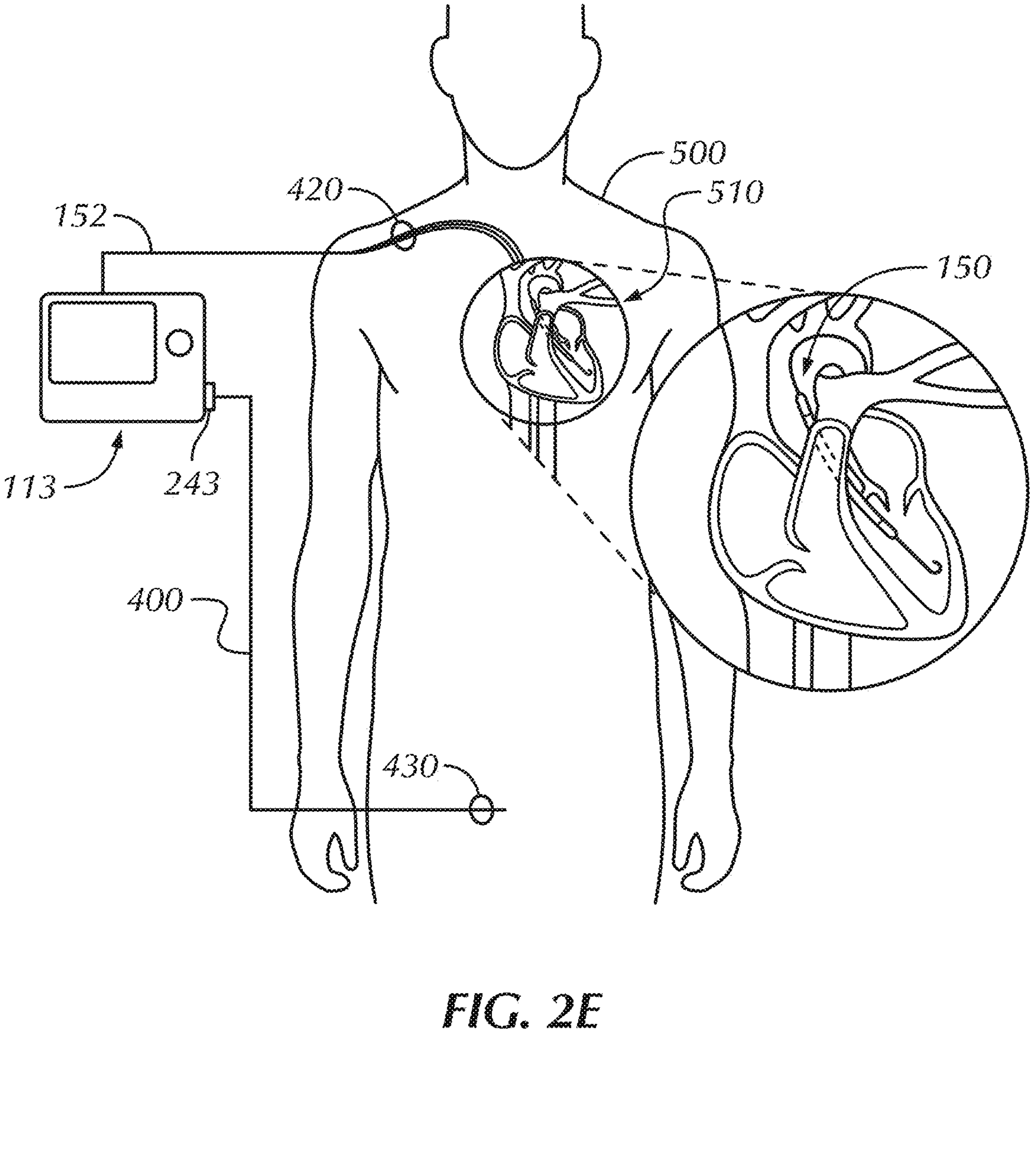

Referring to FIG. 2E, in some embodiments, the catheter or tube 400 also may be operably connected to a patient 500 at a different location 430 than an insertion point 420 of the intravascular blood pump 150, where the catheter or tube 400 is configured to transfer the blood sample from the patient to the first port 243. For example, the intravascular blood pump may be inserted through a jugular vein, while the catheter or tube 400 is operably connected to an access site at a femoral artery.

Figure 2F:
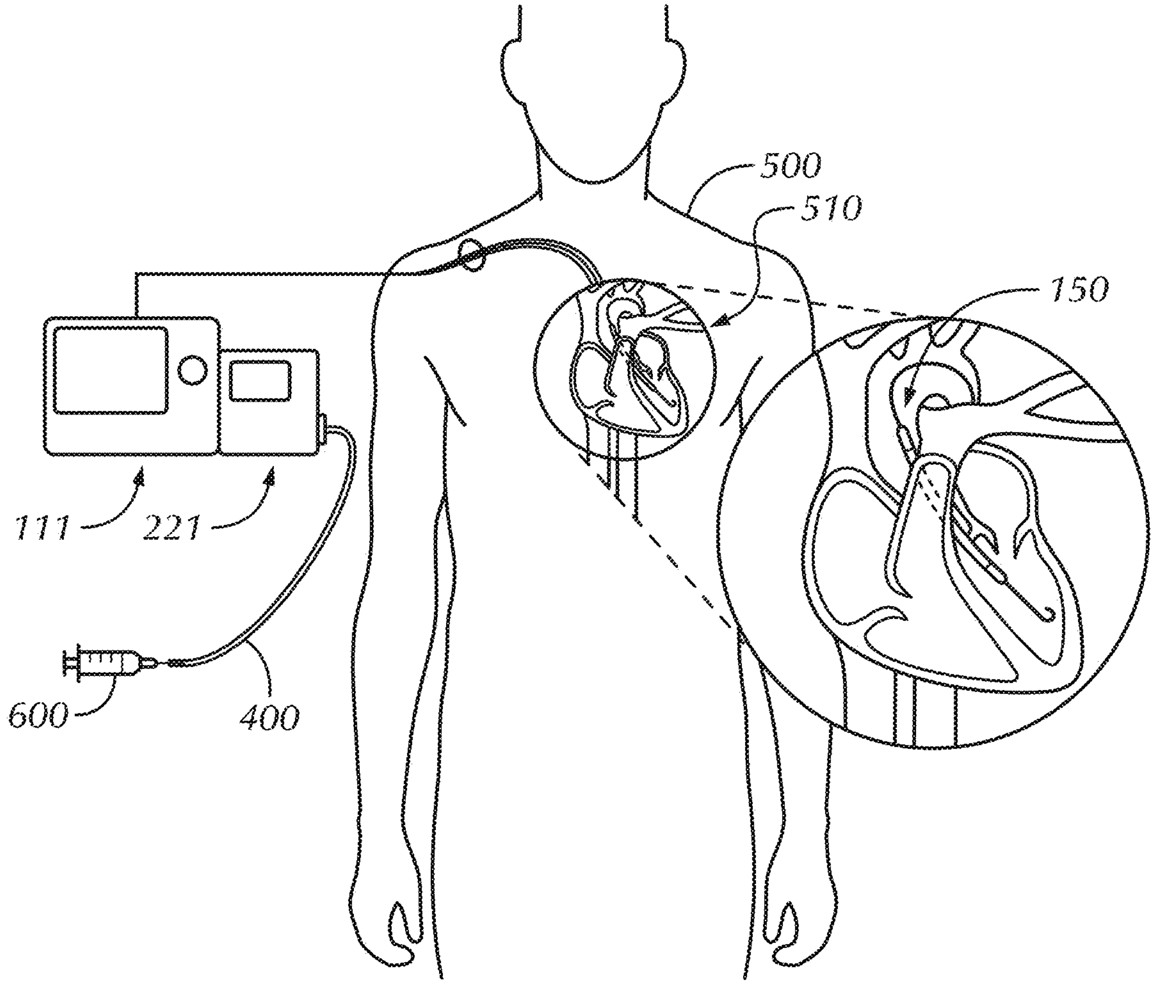
FIG. 2F is an illustration of a system where a blood sample is captured manually and passed to the console.

Referring to FIG. 2F, in some embodiments, the blood sample may be gathered separately and transferred manually to the system (e.g., via the port 243). In some embodiments, the blood sample may be captured using a syringe 600. In some embodiments, the blood sample may then be provided directly to the patient console 111 and/or blood monitoring console 221, and/or may be injected into a tube 400 for delivery to the system 101.

Referring again to FIG. 1, in some embodiments, the system 100 may also include a second port 250 configured to allow blood to exit the housing. In some embodiments, the second port 250 may be connected to a waste stream 330. In some embodiments, the second port 250 may be operably coupled to a container 335 for disposal of biohazardous material.

In some embodiments, the blood monitoring sensor 210 may be configured to sense the blood parameter of the blood sample 300 received in the first port 243.

Figure 3:
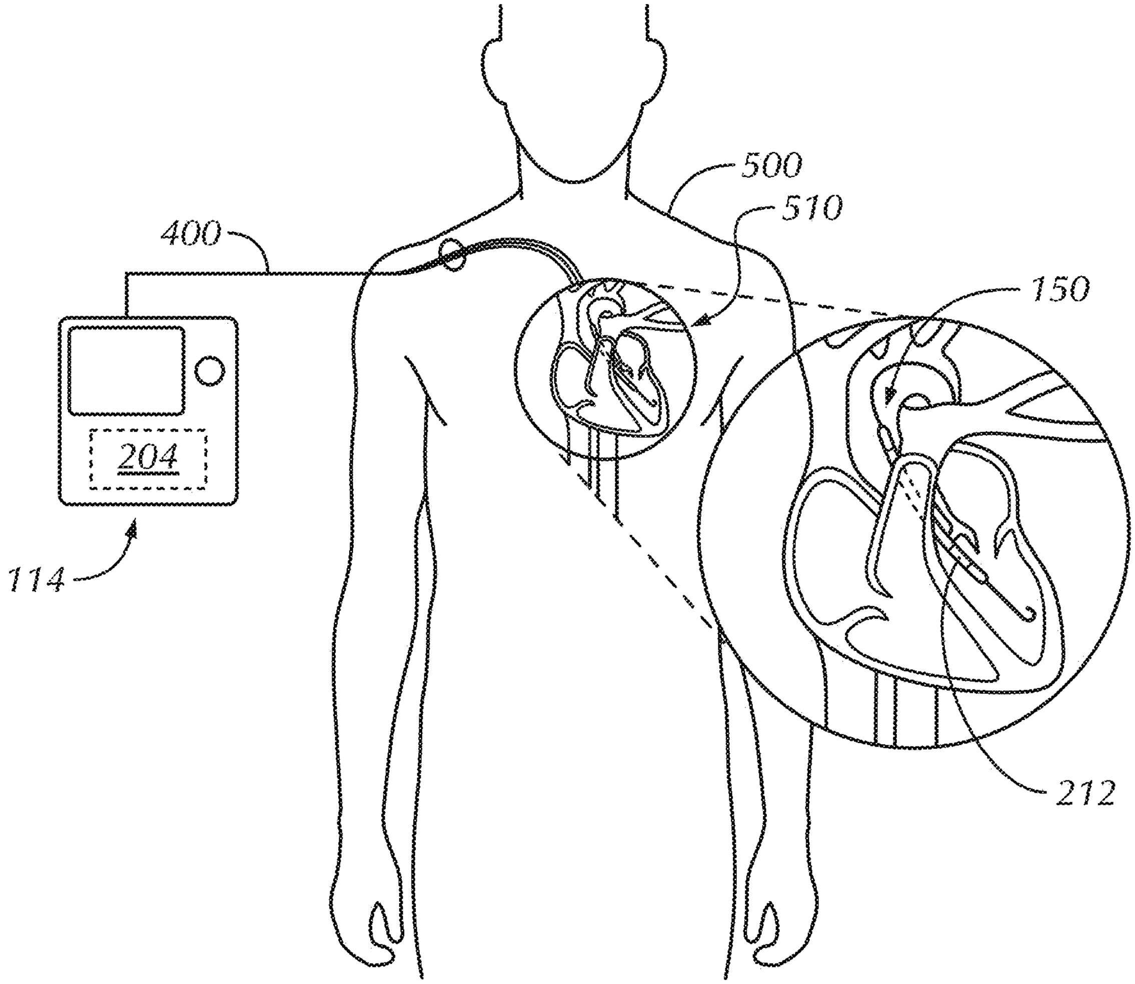
FIG. 3 is an illustration of a system where a blood monitoring sensor is positioned remotely from the console.

Referring to FIG. 3, in some embodiments, a blood monitoring sensor 212 may be disposed in or on the intravascular blood pump 150. In some embodiments, the patient console 114 and/or blood monitoring console may be free of a first port. The system may still comprise a blood monitoring module 204 within the patient console 114 and/or blood monitoring console, but the blood monitoring sensor 212 may be located remotely (here, in or on the blood pump).

As shown in FIG. 3, in some embodiments, information from the blood monitoring sensor 212 may be communicated to the patient console and/or blood monitoring console via a catheter or tube 400 (e.g., via one or more wires). In some embodiments, the catheter or tube 400 may be the same catheter or tube that is operably coupled to the intravascular blood pump 150.

Figure 4:
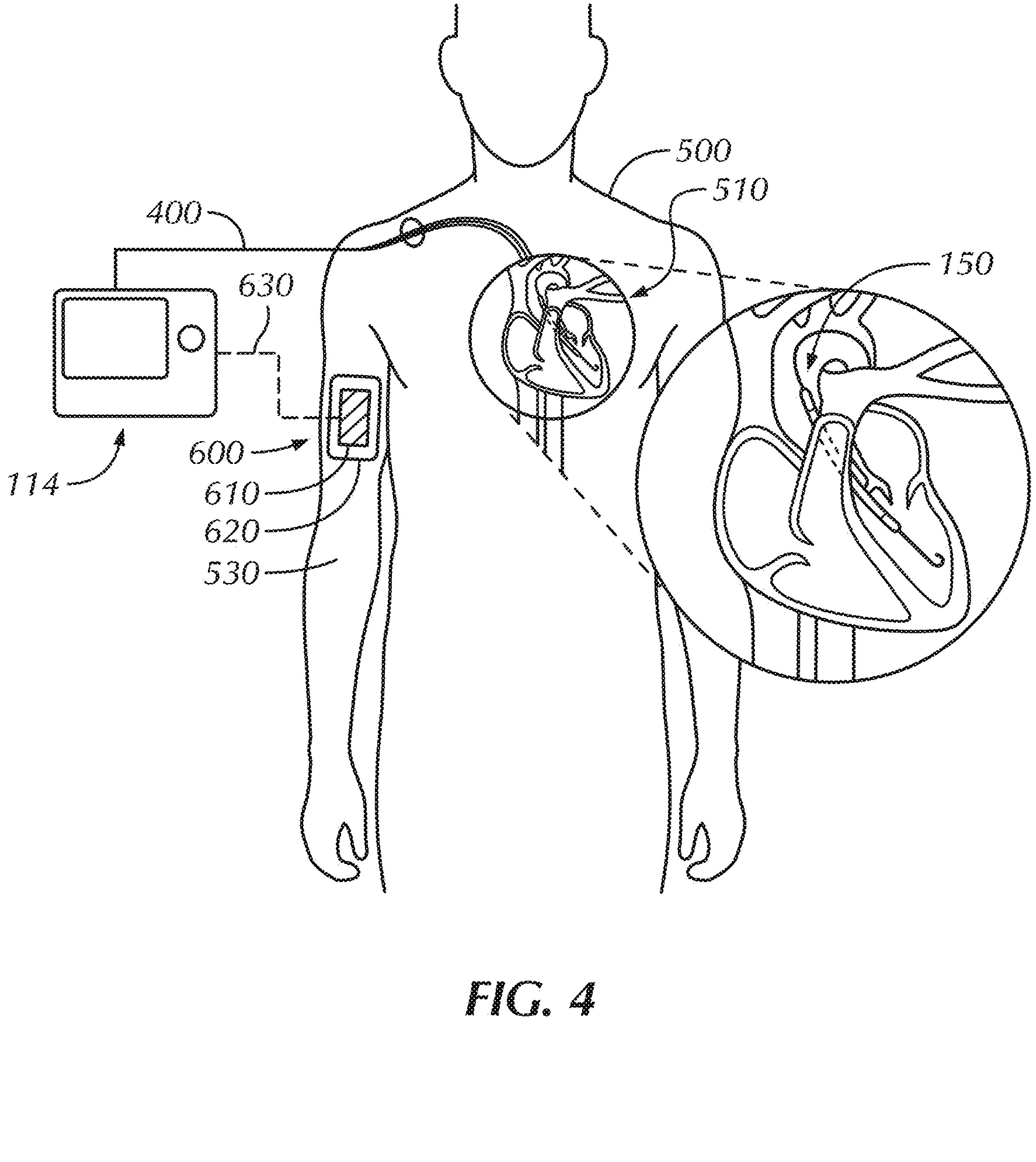
FIG. 4 is an illustration of a system where at least some of the blood monitoring console may be coupled to a patient, rather than to a patient console.

Referring to FIG. 4, in some embodiments, some or all of the blood monitoring console and the sensor may be operably coupled to a patient. In some embodiments, one or more patches 600 may be attached to an arm 530 or other suitable portion of a patient 500. In some embodiments, patch 600 may comprise a substrate 620 that may have a surface that adheres to the skin of the patient. Each patch 600 may, independently, include circuitry 610 that may include some or all of the blood monitoring console and/or sensor (e.g., ref. 200 and 210, respectively, from FIG. 1). For example, in some embodiments, the patch 600 may include a blood monitoring sensor that senses a blood parameter and communicates the parameter to the patient console and/or to the blood monitoring console.

In some embodiments, each patch may be operably coupled 630 to a patient console 114 and/or blood monitoring console. This may be done wired or wirelessly.

Referring again to FIG. 1, in some embodiments, the system 100 may include one or more processors 160, 260. In some embodiments, the pump control module 140 and the blood monitoring module 200 are operably coupled 145 to at least one of the one or more processors 160, 260.

In some embodiments, the system comprises a single processor (e.g., processor 160). In some embodiments, the system comprises plurality of processors including a first processor 160 and a second processor 260. In some embodiments, the pump control module 140 may include the first processor 160. In some embodiments, the blood monitoring module 200 may include the second processor 260.

In some embodiments, the system 100 may include a non-transitory computer readable storage medium 180. In some embodiments, the computer readable storage medium may contain instruction that, when executed by the one or more processors, cause the system to first receive information about a blood sample from a sensor. Then, the system may determine a value of a blood parameter based on the information about the blood sample. And finally, the system may display the value of the blood parameter on the first display screen and/or on a second display screen.

In some embodiments, a sensed blood parameter may be stored on the patient console and/or blood monitoring console. As will be appreciated, in some embodiments, the system also may be operable connected to a cloud-based system (e.g., via one or more wires or wirelessly), which may communicate sensed data from the system. As will be further appreciated, in some embodiments, the information about the blood sample may be sent to the cloud-based system, where the information may be converted into a blood parameter. This blood parameter may thereafter be sent back to the patient console and/or blood monitoring console, where it is disposed on one of the screens.

In some embodiments, the one or more processors are further configured with instructions that, when executed, cause the system to receive the blood sample. For example, if a cartridge or vial containing a blood sample is inserted into the first slot, the system may be configured to cause the vial or cartridge to be recognized as having been inserted and/or detecting whether it includes a blood sample. In some embodiments, the system may be configured to cause at least a portion of the blood sample to contact a blood monitoring sensor. In some embodiments, the processor may be configured to cause a blood sample to be retrieved by an intravascular blood pump. In some embodiments, the processor may be configured to cause the blood sample to be transported to the housing (either the first or second housing, depending on the configuration of the system) via a catheter or tube.

In some embodiments, the one or more processors may be further configured with instructions that, when executed, cause the system to adjust one or more valves for controlling a flow of the blood sample through the system. In some embodiments, this may include, opening or closing a valve in or on the blood pump itself. In some embodiments, this may include opening on closing a valve to a vacuum source, causing blood to be pulled up a tube towards the housing.

Figure 5:
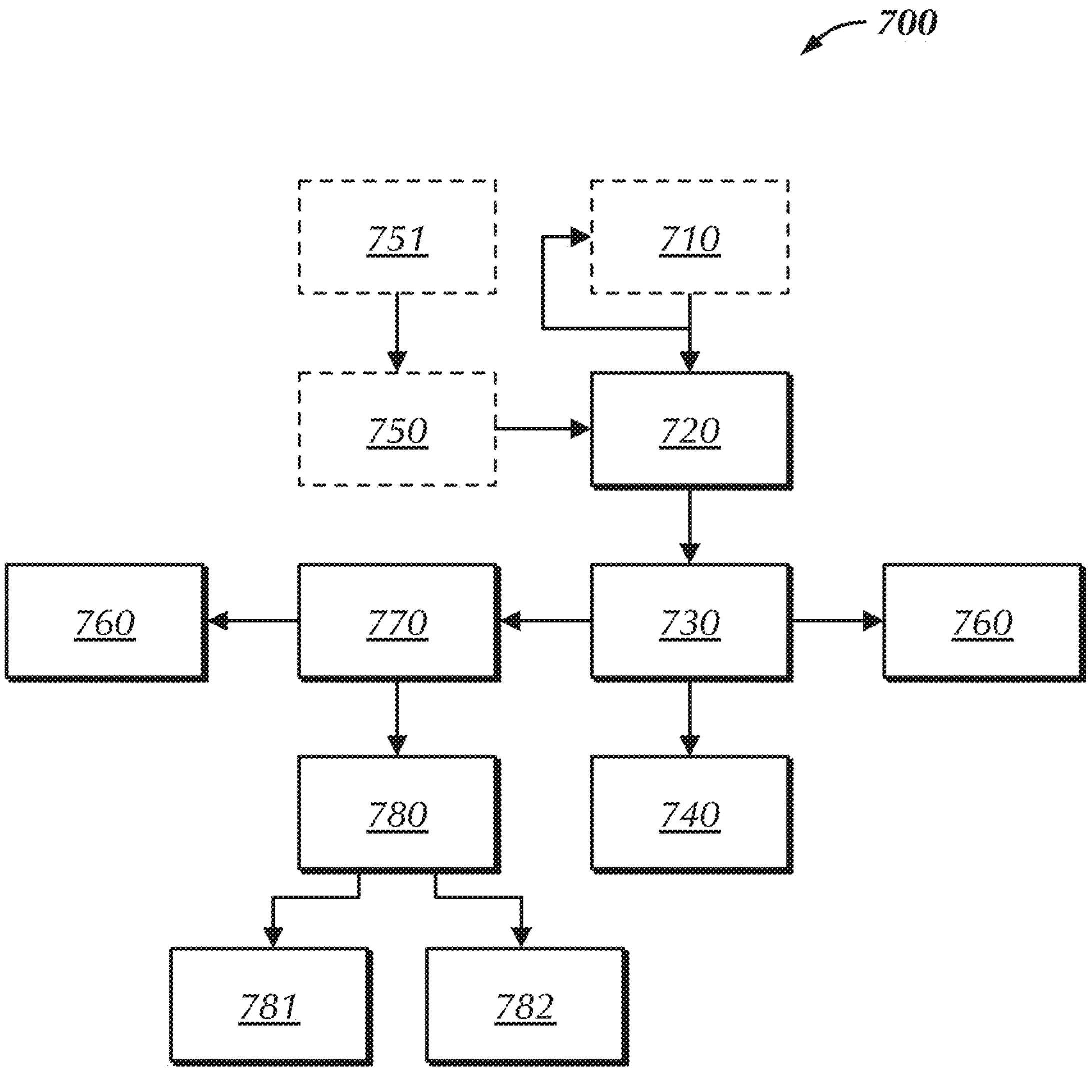
FIG. 5 is a flowchart of an embodiment of a method.

A flowchart of an embodiment of a method can be seen in FIG. 5. There, the method 700 includes operating 710 a blood pump, such as an intravascular blood pump. The blood pump may be operated via a module at least partially disposed in a patient console. This step is shown in FIG. 5 as a recursively occurring step. However, it will be understood that it may occur at any or all other times, and the blood pump may be continuously operated while the rest of the method is being performed. As will be appreciated, although shown with the use of a blood pump, it will be appreciated that the method may not include this step (e.g., if such monitoring were conducted prior to or after use of the blood pump).

As also shown in FIG. 5, the method 700 may include receiving 720 information about a blood sample from a blood monitoring sensor. As will be understood, this may include receiving an analog signal from a sensor, or a digital signal containing sensor information. In some embodiments, this information may be received from a blood monitoring sensor within a blood monitoring console or a patient console (e.g., via port 243 from a vial that is inserted through one or more tubes or catheters). In some embodiments, this information may be received from a blood monitoring sensor in or on a blood pump. In some embodiments, this information may be received from a blood monitoring sensor of a monitoring patch configured to be disposed on a body of a patient.

The method may include determining 730 a value of a blood parameter based on the received blood sample information. The blood parameter may be, or may relate to, blood coagulation. In some embodiments, the blood parameter may include a prothrombin time (PT). In some embodiments, the blood parameter may include an international normalized ratio (INR).

Figure 6:
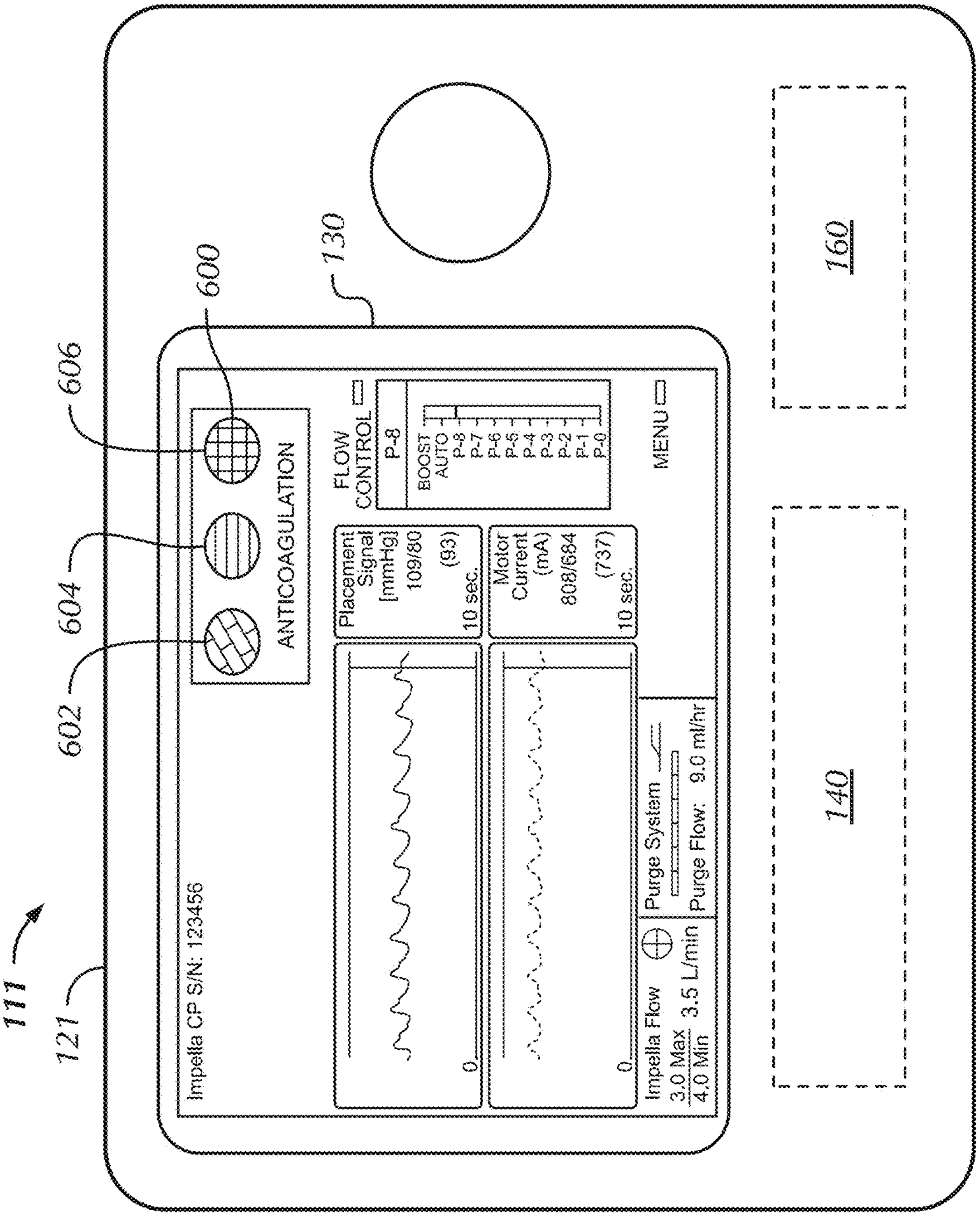
FIG. 6 is a schematic illustration of another embodiment of a system.

The method also may include displaying 740 the value of the blood parameter on a display screen of the patient console and/or the blood monitoring console. In some embodiments, this may include displaying a numeric value of a blood parameter on the display screen. The method also may include displaying a visual indica 600 of the sensed blood parameters. For example, in some embodiments, as shown in FIG. 6, the display may be configured to display a colored indicia (e.g., red 602, yellow 604, green 606) depending upon whether the blood parameter falls inside (or outside) set threshold values. A threshold line may be displayed in some embodiments. As will be appreciated, such visual indicia also may serve as an alert to the physician, depending upon the shown colored indicia. As will be appreciated, the visual indicia may include sliders or other suitable indicia in some embodiments.

The method may also include receiving 750 a blood sample at one of a patient console and a blood monitoring console. Upon receipt, a blood monitoring sensor, which may be part of a blood monitoring module, may be utilized to detect or sense information about the blood sample. In some embodiments, receiving the blood sample may include receiving the blood sample in a first port disposed on the patient console or the blood monitoring console. In some embodiments, the sample may be in a cartridge or vial. In some embodiments, the sample may be provided via a catheter or tube. In some embodiments, the first port may be configured to be operably coupled to a catheter or tube. In some embodiments, the catheter may be configured to transfer the blood sample from the patient to the first port. In some embodiments, the method may include obtaining 751 the blood sample. In some embodiments, this may be done using the intravascular blood pump. In some embodiments, this may be done manually (e.g., drawing blood from a patient using a needle/syringe).

The method may also include predicting 770 at least one other parameter using the value of the blood parameter. In some embodiments, a value of a sensor coupled to the blood pump may also be used to predict the at least one other parameter. In some embodiments, a trained machine learning algorithm may be used to predict at least one other parameter. In some embodiments, the trained machine learning algorithm may further use a value from a thromboelastogram to predict the at least one other parameter. In some embodiments, the other parameter may include a prediction of heart failure that is made while the blood pump is positioned at least partially within a left ventricle. In some embodiments, the at least one other parameter may include a prediction of a bleeding condition.

The method may also include controlling providing an alert 760 to a clinician based upon the value of the blood parameter, or parameter predicted using the value of the blood parameter. For example, if the value is outside a desired threshold value, a clinician may receive an alert to (e.g., to provide more anticoagulant). In other embodiments, the alert may suggest that a clinician modify operation of the blood pump. For example, the blood parameter is an increasing percentage of blood coagulation, it may be useful to attempt to reduce the risk of thrombus formation by adjusting the speed of the pump, thereby adjusting the flow characteristics of blood through the blood pump. As will be appreciated, in some embodiments, the method may include controlling the blood pump (e.g., by adjusting the speed of the pump) in response to the blood parameter.

The method may also include determining 780 an anticoagulation measure based on the predicted at least one other parameter. The method may also include displaying 781 the anticoagulation measure and/or automatically enacting 782 the anticoagulation measure. In some embodiments, the anticoagulation measure comprises a dosage of an anticoagulant. In some embodiments, the anticoagulation measure comprises a dosage of heparin or protamine. For example, the method may include determining an appropriate dosage of heparin.

Similar to the blood parameter, in some embodiments, the method may include displaying the anticoagulation measure on the display. In some embodiments, this may include displaying a numerical value on the display. As shown in FIG. 6, this may include displaying visual indicia 600 (e.g., the colored indicia—red 602, yellow 604, green 606) depending upon whether the anticoagulation measure falls inside (or outside) set threshold values. As will be appreciated, such visual indicia also may serve as an alert to the physician, depending upon the shown indicia. For example, in some embodiments, this may alert a clinician that more (or less) anticoagulants may be needed for a patient depending upon the sensed blood parameter (and displayed anticoagulation measure). As will be appreciated, the visual indicia may include sliders or other suitable indicia in some embodiments.

Those skilled in the art will recognize or be able to ascertain using no more than routine experimentation many equivalents to the specific embodiments of the invention described herein. Such equivalents are intended to be encompassed by the following claims.

What is claimed is:

1. A system comprising:

a patient console having a first housing with a first display screen;

a pump control module at least partially disposed within the first housing, the pump control module configured to control an intravascular blood pump and display information about the blood pump on the display screen; and a blood monitoring module configured to derive a value of a blood parameter from information received from a blood monitoring sensor about a blood sample and display the value of the blood parameter on the first display screen and/or on a second display screen, wherein the system further comprises a plurality of processors, including a first processor and a second processor, the pump control module further comprising the first processor and the blood monitoring module further comprising the second processor; and/or wherein the blood monitoring module is within the first housing; and/or wherein the system further comprises a blood monitoring console having a second housing with the second display screen, wherein the blood monitoring module is disposed in the second housing; and/or wherein the system further comprises a first port configured to receive the blood sample; and/or wherein the blood parameter comprises a prothrombin time (PT), an activated clotting time (ACT), a clot propagation rate, a clot strength, a rate of clot breakdown, a platelet mapping, a functional fibrinogen, and/or a fibrin polymerization; and/or wherein the value related to the blood parameter comprises an international normalized ratio (INR).

2. The system according to claim 1, wherein the pump control module is operably coupled to at least one of the plurality of processors, and the blood monitoring module is operably coupled to the processor.

3. The system according to claim 1, wherein the blood monitoring console is coupled to the patient console.

4. The system according to claim 3, wherein the blood monitoring console is removably coupled to the first housing.

5. The system according to claim 3, wherein the blood monitoring module is disposed at least partially in the first housing.

6. The system according to claim 3, wherein the processor is disposed only within the first housing.

7. The system according to claim 1, wherein the blood monitoring sensor is configured to sense the blood parameter of the blood sample received in the first port.

8. The system according to claim 1, wherein the first port is configured to removably receive a cartridge containing the blood sample.

9. The system according to claim 1, wherein a catheter is operably connected to a patient at a different location than an insertion point of the intravascular blood pump, and wherein the catheter is configured to transfer the blood sample from the patient to the first port.

10. The system according to claim 9, wherein the catheter is operably connected to the intravascular blood pump, wherein the catheter is configured to transfer the blood sample from the patient to first port.

11. The system according to claim 1, further comprising a second port configured to allow blood to exit the housing.

12. The system according to claim 1, wherein the blood monitoring sensor is disposed on the intravascular blood pump.

13. The system according to claim 1, wherein the blood parameter comprises or relates to blood coagulation.

14. A system, comprising:

a pump control module configured to control an intravascular blood pump; and one or more processors operably communicating with the pump control module, the one or more processors being within a patient console and/or a blood monitoring console, and the one or more processors configured with instructions that, when executed by the one or more processors, cause the system to:

receive information about a blood sample from a sensor;

determine a value of a blood parameter based on the information about the blood sample; and display the value of the blood parameter on the first display screen and/or on a second display screen, wherein the one or more processors comprises a plurality of processors, including a first processor and a second processor, the pump control module comprising the first processor and the blood monitoring module comprising the second processor; and/or wherein the blood monitoring module is within a first housing of the patient console; and/or wherein the blood monitoring console comprises a second housing with a second display screen, wherein a blood monitoring module is disposed in the second housing; and/or wherein the system further comprises a first port configured to receive the blood sample; and/or wherein the blood parameter comprises a prothrombin time (PT), an activated clotting time (ACT), a clot propagation rate, a clot strength, a rate of clot breakdown, a platelet mapping, a functional fibrinogen, and/or a fibrin polymerization; and/or wherein the value related to the blood parameter comprises an international normalized ratio (INR).

15. A method comprising:

receiving information about a blood sample from a blood monitoring sensor;

determining a value of a blood parameter based on the received blood sample information, wherein the blood parameter is or relates to blood coagulation;

displaying the value of the blood parameter on a display screen of a patient console and/or a blood monitoring console; and operating a blood pump via a pump control module that is at least partially disposed in the patient console, wherein the pump control module comprises a first processor and a blood monitoring module comprises a second processor; and/or wherein the blood monitoring module is within a first housing of the patient console; and/or wherein the blood monitoring console comprises a second housing with a second display screen, wherein a blood monitoring module is disposed in the second housing; and/or wherein the method further comprises receiving the blood sample at a port of the patient console or blood monitoring console; and/or wherein the blood parameter comprises a prothrombin time (PT), an activated clotting time (ACT), a clot propagation rate, a clot strength, a rate of clot breakdown, a platelet mapping, a functional fibrinogen, and/or a fibrin polymerization; and/or wherein the value related to the blood parameter comprises an international normalized ratio (INR).

* * * * *